(12) United States Patent
Burke et al.

(10) Patent No.: US 8,545,477 B2
(45) Date of Patent: Oct. 1, 2013

(54) MULTIPLE RESERVOIR IMPLANTABLE DRUG INFUSION DEVICE AND METHOD

(75) Inventors: Paul F. Burke, Bellingham, MA (US); Joshua L. Buckman, Newton, MA (US); Patrick J. O'Connor, North Attleboro, MA (US)

(73) Assignee: Flowonix Medical Incorporated, Mt. Olive, NJ (US)

( * ) Notice: Subject to any disclaimer, the term of this patent is extended or adjusted under 35 U.S.C. 154(b) by 679 days.

(21) Appl. No.: 12/288,659

(22) Filed: Oct. 22, 2008

(65) Prior Publication Data

US 2010/0089487 A1 Apr. 15, 2010

Related U.S. Application Data

(62) Division of application No. 12/074,570, filed on Mar. 5, 2008.

(51) Int. Cl.
- *A61M 31/00* (2006.01)
- *A61M 1/00* (2006.01)
- *A61M 37/00* (2006.01)
- *A61M 5/00* (2006.01)

(52) U.S. Cl.
USPC ............ 604/502; 604/153; 604/141; 604/246

(58) Field of Classification Search
USPC ............... 604/890.1, 891.1, 131, 65–67, 151, 604/246, 140, 141, 200, 502
See application file for complete search history.

(56) References Cited

U.S. PATENT DOCUMENTS

| | | | |
|---|---|---|---|
| 4,193,397 A | 3/1980 | Tucker et al. | 128/207.19 |
| 4,258,711 A * | 3/1981 | Tucker et al. | 604/502 |
| 4,838,887 A * | 6/1989 | Idriss | 604/891.1 |
| 5,049,141 A | 9/1991 | Olive | 604/891.1 |
| 5,281,210 A | 1/1994 | Burke et al. | 604/891.1 |
| 6,764,472 B1 | 7/2004 | Burke et al. | 604/288.04 |
| 7,083,593 B2 | 8/2006 | Stultz | 604/65 |
| 7,108,686 B2 | 9/2006 | Burke et al. | 604/891.1 |
| 7,192,414 B2 | 3/2007 | Stultz | 604/93.01 |
| 2003/0130645 A1* | 7/2003 | Brengle et al. | 604/500 |
| 2004/0082908 A1* | 4/2004 | Whitehurst et al. | 604/67 |
| 2005/0070875 A1 | 3/2005 | Kulessa | 604/500 |

(Continued)

OTHER PUBLICATIONS

International Search Report and Written Opinion dated Mar. 17, 2009.

(Continued)

*Primary Examiner* — Kevin C Sirmons
*Assistant Examiner* — William Carpenter
(74) *Attorney, Agent, or Firm* — The Marbury Law Group, PLLC

(57) ABSTRACT

Multiple reservoir implantable valve accumulator pump for the delivery of medication, and method of infusate delivery. The apparatus includes at least first and second infusate reservoirs in a common pressure chamber, each in fluid communication with a metering assembly. The metering assembly includes an accumulator that is preferably a fixed volume accumulator having an inlet and an outlet. A first valve is in fluid communication with the first infusate reservoir and an inlet of the accumulator, and a second valve is in fluid communication with the second infusate reservoir and an inlet of the accumulator. An outlet valve is in fluid communication with the outlet of the accumulator. The accumulator can be filled with infusate from the first and second infusate reservoirs sequentially, can be filled from the first infusate reservoir multiple times consecutively, the second infusate reservoir multiple times consecutively, or any combination or permutation thereof.

4 Claims, 6 Drawing Sheets

(56) References Cited

U.S. PATENT DOCUMENTS

| | | | |
|---|---|---|---|
| 2005/0277912 A1* | 12/2005 | John | 604/890.1 |
| 2006/0271021 A1 | 11/2006 | Steinbach | 604/891.1 |
| 2006/0271022 A1 | 11/2006 | Steinbach | 604/891.1 |
| 2007/0073230 A1 | 3/2007 | Jasperson et al. | 604/131 |

OTHER PUBLICATIONS

Office action dated Sep. 16, 2008 (in related U.S. Appl. No. 11/906,826).

* cited by examiner ated in a typical configuration, rely on a liquid/vapor equilibrium to maintain constant pressure on the drug which is housed therein so that the drug flows through a capillary (flow restrictor) in order to maintain a constant flow rate. Such devices are used in a variety of medical applications, for example, to dispense chemotherapy at a relatively constant flow rate. As background to the Fluent™ device are U.S. Pat. Nos. 7,108,686 and 6,764,472.

MULTIPLE RESERVOIR IMPLANTABLE DRUG INFUSION DEVICE AND METHOD

This application is a divisional of U.S. patent application Ser. No. 12/074,570 filed Mar. 5, 2008, the disclosure of which is incorporated herein by reference

BACKGROUND OF THE INVENTION

This invention relates to implantable infusion pumps for the dispensing of infusates. In particular, it relates to a pump operating at positive pressure to dispense medication from multiple reservoirs in accordance with different specified flow rates. The device is capable of delivering easily and precisely dosed medication from any one or any combination of two or more reservoirs without complex pumping and flow control mechanisms and has the capability of mixing and/or diluting medications.

Implantable infusion pumps are currently used for a variety of medical purposes. Two classes of such commercially acceptable are generally referred to as "constant flow" and "programmable" pumps. Typical of the constant flow device is the Fluent™ pump. Constant flow devices are implanted in the human body and, in a typical configuration, rely on a liquid/vapor equilibrium to maintain constant pressure on the drug which is housed therein so that the drug flows through a capillary (flow restrictor) in order to maintain a constant flow rate. Such devices are used in a variety of medical applications, for example, to dispense chemotherapy at a relatively constant flow rate. As background to the Fluent™ device are U.S. Pat. Nos. 7,108,686 and 6,764,472.

There are medical conditions where a patient requires an adjustment in the dosage or requires a bolus infusion and as such, constant flow pumps are inadequate. Typical examples are the use of implantable pumps to treat chronic back pain and/or spasticity as seen in multiple sclerosis. In such cases a programmable pump is used to achieve proper flow rates over the spectrum of desired rates. An example of such a device is the Prometra® implantable programmable pump. The pump has a refillable drug reservoir that is maintained at constant pressure vapor. The reservoir communicates with a medication metering assembly consisting of a fixed volume accumulator positioned between a pair of valves. The valves alternately open and close to admit medication from the reservoir into the accumulator and to dispense a precise volume spike to an outlet catheter. The unit is externally programmed. As background to the Prometra® pump is U.S. Pat. No. 5,049,141.

Multiple medications are often put into implantable pumps to treat certain specific conditions. For example, morphine may be used to treat the nociceptive pain and a local anesthetic (such as bipuvicaine) may be used to treat a neuropathic pain component. The use of multiple medications in single drug reservoir presents difficult clinical and medical device challenges. The mixture of drugs may present drug stability issues and a complex dosing challenge given the varying concentration and administration rates for each drug.

In U.S. Patent Publication No. 2007/0073230 to Jasperson et al., entitled "Drug Infusions System with Multiple Medications", a system intended to minimize the danger for confusion and error in dosing multiple drugs from a common reservoir is described. More than one drug in the reservoir of the implantable infusion device substantially increases patient dosing difficulties. The clinician not only must program the device to perform a series of steps in order to deliver one drug to the patient, but must also take into account the affect of creating or modifying a program for one of the drugs on the delivery of all other drugs also contained within the same reservoir. Jasperson's system determines the resultant dose of a secondary dose based upon changes in primary drug dosage rates and displays it to the clinician.

In U.S. Pat. No. 7,083,593 and U.S. Pat. No. 7,192,414 to Stulz, each entitled, "Programmable Implantable Pump with Accessory Reservoirs and Multiple Independent Lumen Catheter", an implantable pump with multiple chambers or reservoirs for storing drugs, each coupled to a dedicated pumping mechanism and outlet catheter is disclosed. The device does not permit the mixing and/or dilution of medication. Separate pumping mechanisms affect device reliability and manufacturing efficiencies.

Tucker et al. in U.S. Pat. Nos. 4,193,397 and 4,258,711, entitled, "Infusion Apparatus And Method", disclose a dual reservoir implantable pump with an accumulator—a basal reservoir containing medication of a certain dosage and a smaller bolus reservoir containing high concentrate medication. The basal reservoir discharges medication at a constant specified rate. The bolus reservoir discharges the high concentration of medication to a smaller accumulator and, at a specified time, the accumulator discharges the bolus dose into a chamber where it is combined with the basal medication discharge. Combined dosing is not simply the instantaneous sum of the basal and bolus rates, it is a complex function of reservoir volumes, infusate concentrations, flow path resistance, mixing chamber volume, outlet tube volume and valve-on time. The bolus dose cannot be administered separately unless the basal reservoir is empty nor can it be mixed or diluted by the basal medication.

In U.S. Patent Publication No. 2005/0070875 to Kulessa, entitled, "Two-Compartment Reduced Volume Infusion Pump", a dual reservoir infusion pump is disclosed wherein small amounts of concentrated medication are mixed and diluted in a mixing chamber with a carrier prior to being released into the patient. Various challenges and methods to control dosages are disclosed including: diameter of flow path conduits, flow restrictors for either or both medication and/or carrier pathways, and discharge rates. Dosing flexibility is therefore limited by the selection of manufacturing components. Separate pumping mechanisms affect device and manufacturing efficiencies. The pump is not designed to deliver multiple drugs.

In U.S. Patent Publication No. 2006/0271022, to Steinbach and Lederer, entitled, "Multi-Reservoir Implantable Pump with Variable Flow Rate Capabilities", a constant flow pump with two reservoirs capable of infusing two different drugs is described. It is a three chamber device with an outlet in fluid communication with the two chambers that are drug reservoirs. One of the chambers is pressurized and juxtaposed between the drug reservoirs. A flow restrictor leading from each reservoir regulates the flow of medication from that reservoir to the patient. Reservoir flows rates cannot be changed and they are variable only to the extent an election is made to use one or the other drug reservoir (if the restrictors are different) or if both chambers are filled with drugs. A mixing and/or dilution mechanism is not included.

There is a need in the art for an implantable infusion device with multiple medication reservoirs that is capable of delivering easily dosed medication from any one or any combination of reservoirs without complex pumping and flow control mechanisms and which optionally has the capability of mixing and/or diluting medications.

SUMMARY OF THE INVENTION

A multiple reservoir implantable valve accumulator pump for the delivery of medication is disclosed. The apparatus includes at least first and second infusate reservoirs, each in fluid communication with a metering assembly. The metering assembly includes an accumulator that is preferably a fixed volume accumulator having an inlet and an outlet. A first valve is in fluid communication with the first infusate reservoir and an inlet of the accumulator, and a second valve is in fluid communication with the second infusate reservoir and an inlet of the accumulator. An outlet valve is in fluid communication with the outlet of the accumulator. Infusate from the first infusate reservoir is introduced into the accumulator by opening the first valve while the outlet valve is closed (and while the second valve is closed). The accumulator can then be emptied by closing the first valve and opening the outlet valve. Infusate from the second infusate reservoir is introduced into the accumulator by opening the second valve while the outlet valve is closed (and while the first valve is closed). The accumulator can then be emptied by closing the first valve and opening the outlet valve. The accumulator can be filled with infusate from the first and second infusate reservoirs sequentially, can be filled from the first infusate reservoir multiple times consecutively, the second infusate reservoir multiple times consecutively, or any combination or permutation thereof. Preferably the multiple reservoirs are located in a common pressure chamber supplying the driving force; that is, a single pressure chamber containing propellant is used to drive both reservoirs, thereby effectively reducing the size of the device.

In its method aspects, the present invention includes independently introducing infusate into an accumulator from at least two separate infusate sources. In certain embodiments, the method includes providing a first infusate reservoir containing a first infusate, a second infusate reservoir containing a second infusate, and independently introducing the first and second infusates from their respective infusate reservoirs into an accumulator. To that end, a first valve in fluid communication with the first infusate reservoir and with the accumulator controls the flow of the first infusate from the first infusate reservoir to the accumulator, and a second valve in fluid communication with the second infusate reservoir and with the accumulator controls the flow of the second infusate from the second infusate reservoir to the accumulator. Once the accumulator is filled from one or the other infusate reservoir, the first and second valves are closed, and an outlet valve in fluid communication with an outlet of the accumulator is opened to allow infusate to flow from the accumulator to the desired delivery point in a patient, usually through a suitable catheter or the like. The accumulator is then filled again, either from the first or the second infusate reservoir, by closing the outlet valve and opening the either the first or second valve, as the case may be. Both reservoirs preferably are driven from a common pressure chamber.

DETAILED DESCRIPTION OF THE INVENTION

Figure 1:
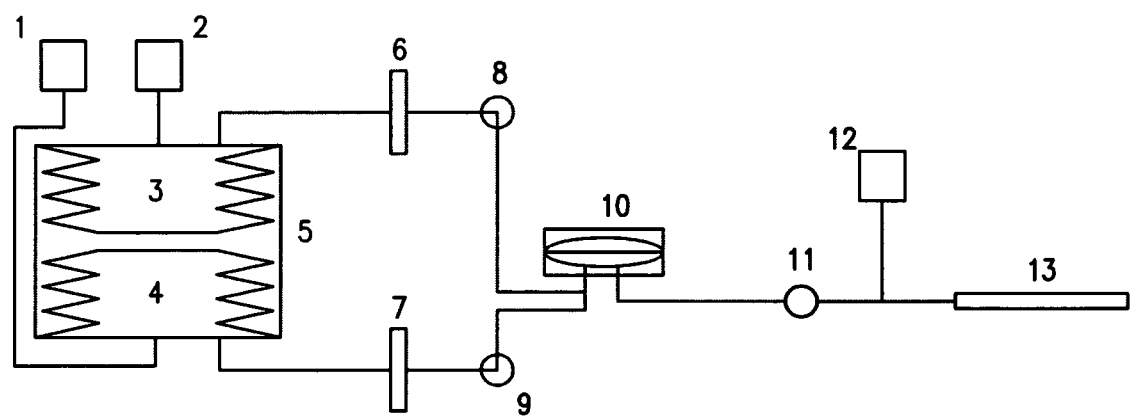
FIG. 1 is a schematic view of the implantable infusion device in accordance with certain embodiments.

In certain embodiments, the invention relates to a positive pressure programmable valve pump comprising two drug reservoirs that optionally may be constant pressure reservoirs. Turning now to FIG. 1, there is shown schematically a sealed housing 5 that contains two bellows that respectively define reservoir 3 and reservoir 4. These reservoirs are isolated from each other by the bellows. Each reservoir is preferably rechargeable with infusate, such as by respective septa 1, 2. Each reservoir includes an internal volume that is adapted to contain medicament or other fluid to be infused to a patient. A suitable material of construction for each bellows is titanium. Although preferably the bellows are oppositely disposed in order to minimize size and uniformly use the same pumping chamber, they could be positioned differently with respect to each other (or in separate housings) without departing from the spirit and scope of the invention. The bellows are collapsible. External of each bellows and within housing 5 is a single source pressure or pump chamber that contains a fluid, such as a two-phase fluid or propellant having a significant vapor pressure at normal body pressure so that it compresses each bellows and causes the fluid in each reservoir 3, 4 to exit an outlet of the housing 5 upon valve actuation.

The reservoirs 3, 4 are each capable of individually containing the total volume of the overall reservoir (e.g., reservoir 3=100%, reservoir 4=0%) or a corresponding ratio of the total volume of the overall reservoir (e.g., reservoir 3=75%, reservoir 4=25%).

Infusate exiting the housing 5 from reservoir 3 flows through filter 6, the flow being regulated by a normally closed valve 8 in fluid communication with the bellows 3 and an inlet of the accumulator 10. Similarly, infusate exiting the housing 5 from the reservoir 4 flows through filter 7, and the flow is regulated by a normally closed valve 9 in fluid communication with the bellows 4 and an inlet of the accumulator. The accumulator, the valves 8 and 9, and a normally closed outlet valve 11 in fluid communication with an outlet of the accumulator, generally define a medication metering assembly. The valves 8 and 9 can be actuated simultaneously to fill the accumulator with infusate from both reservoirs, but preferably are actuated at different times to fill the accumulator, which is then emptied before it is filled again with infusate from one or the other reservoir. The valves 8, 9 and 11 are in fluid isolation with respect to each other. The outlet of the accumulator 10 communicates with a catheter 13 or the like that delivers the infusate to the delivery site in the patient in a conventional manner, upon closing the valves 8 and/or 9 and opening outlet valve 11.

In certain embodiments, the accumulator 10 is a fixed volume accumulator and includes a chamber housing a diaphragm. The diaphragm provides a barrier between a gas portion of the chamber, and a liquid (infusate) portion of the chamber. When the chamber is devoid of liquid (e.g., the infusate has been discharged), the diaphragm is in a resting position. Upon opening an inlet valve, infusate under pressure enters the fluid portion of the chamber and urges the diaphragm against the bias of the gas in a first (e.g., upward) direction to fill the chamber with infusate. The inlet valve is then closed, and upon opening the outlet valve, the gas urges the diaphragm in a second (e.g., downward) direction, forcing the infusate out of the chamber. Alternately valve 8 and/or 9 opens and outlet valve 11 closes to admit medication from a reservoir into the accumulator, followed by closure of the valves 8 and 9 and opening of valve 11 to dispense a precise volume spike of medication to the point of delivery such as via an outlet catheter 13. An access port 12 may be provided to afford direct fluid access to the patient via the catheter 13.

Figure 4:
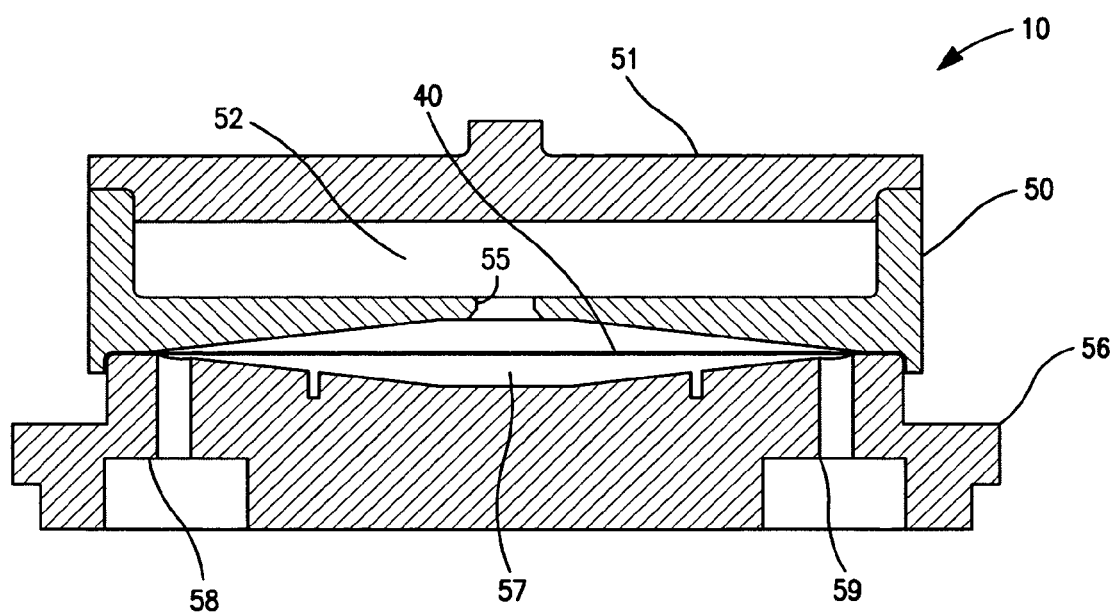
FIG. 4 is a cross-sectional view of an accumulator in accordance with certain embodiments.
Figure 5:
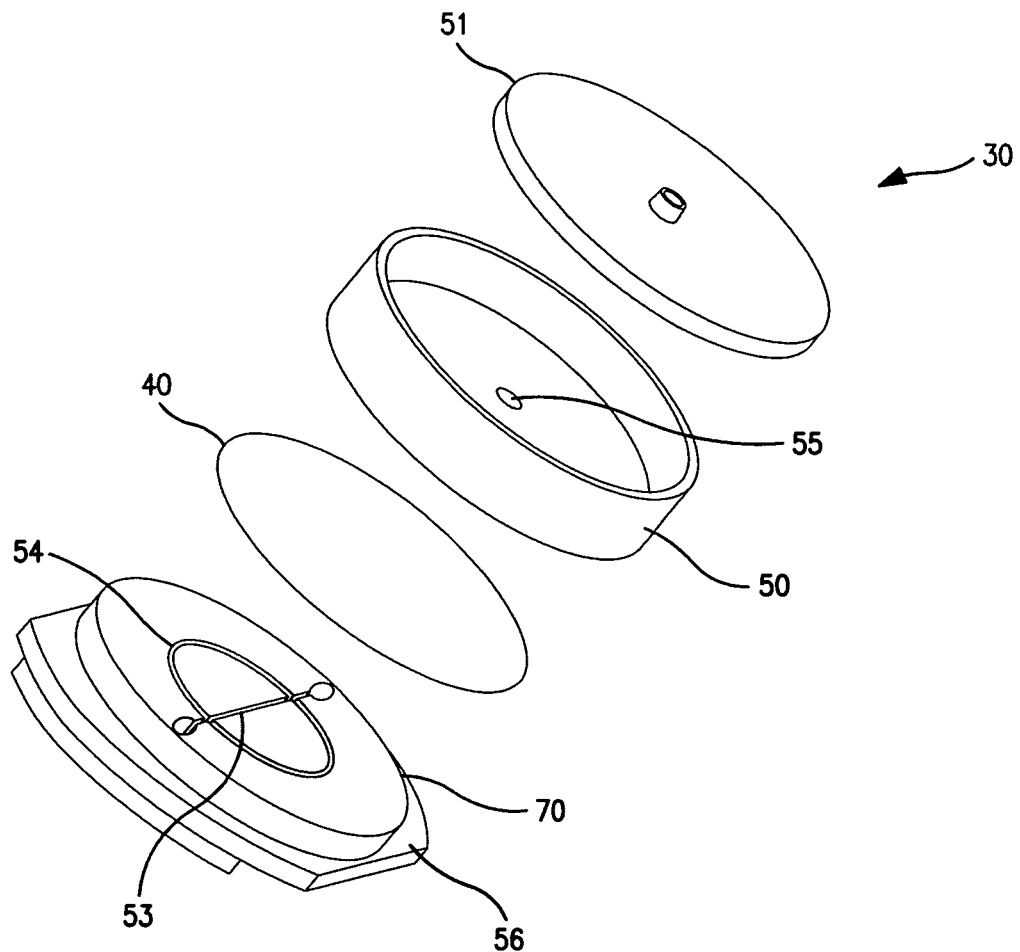
FIG. 5 is an exploded perspective view of an accumulator in accordance with certain embodiments.

In certain embodiments, in order to improve the accuracy of the pump and to increase pumping volume while optimizing the overall size and energy usage of the pump, a two-way diaphragm accumulator is used, such as that disclosed in co-pending application Ser. No. 11/906,826 filed on Oct. 7, 2007, the disclosure of which is hereby incorporated by reference. Specifically, upon opening an inlet valve, infusate under pressure enters the fluid portion of the chamber and urges the diaphragm against the bias of the gas in a first (e.g., upward) direction to introduce infusate into the chamber. The inlet valve is then closed, and optionally, the second inlet valve is opened to similarly introduce infusate into the chamber (the inlet valves could be opened simultaneously if desired). Once the inlet valves are both closed, upon opening the outlet valve, the gas urges the diaphragm in a second (e.g., downward) direction, forcing the infusate out of the chamber. FIGS. 4 and 5 illustrate this embodiment. The accumulator 10 includes a housing 50, which together with cap 51, defines a sealed gas chamber 52. The cap 51 is attached to the housing 50 by any suitable means, such as laser welding. A suitable gas is sealed, under positive pressure, in the gas chamber 52. The gas chamber 52 is in fluid communication with diaphragm chamber 57 via a port 55 in the housing 50. The bottom surface of the housing 50 is configured and positioned to serve as a mechanical stop for the diaphragm 50 when the diaphragm 50 is in the up (fill) position.

Affixed to the housing 50 is a faceplate 56. Preferably the edges of the diaphragm 40 are sandwiched between the housing 50 and faceplate 56 as shown, and the assembly is sealed, such as by laser welding. The volume between the housing 50 and faceplate 56, containing the diaphragm 40, defines the diaphragm chamber 57. The diaphragm 40 thus provides a barrier, separating the gas side (e.g., above the diaphragm) from the fluid side (e.g., below the diaphragm) in the accumulator 10. Faceplate 56 also includes a fluid inlet port 58 that provides fluid communication between inlet valve 8 and the diaphragm chamber 57, and fluid outlet port 59 that provides fluid communication between outlet valve 11 and the diaphragm chamber 57.

Figure 6:
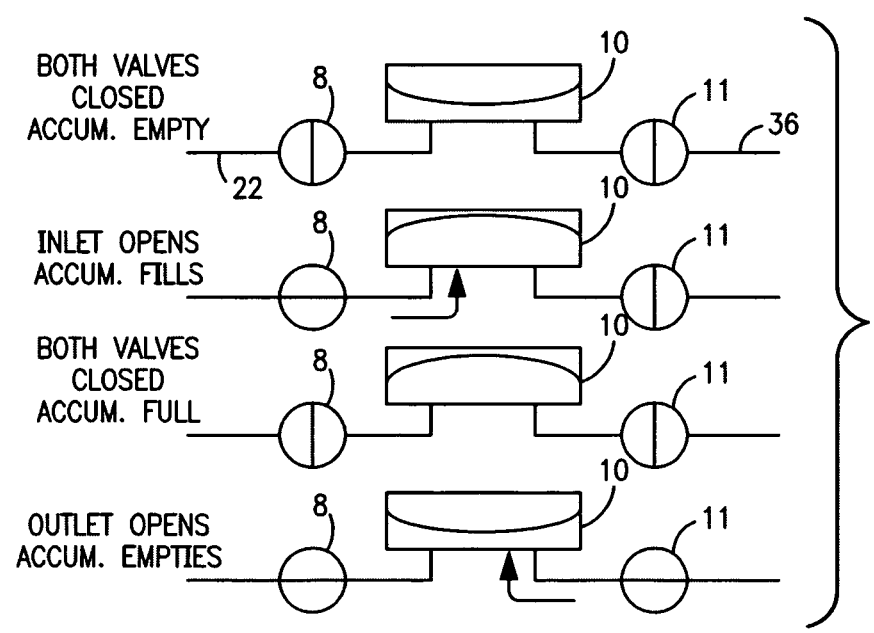
FIG. 6 is a schematic diagram of an accumulator having a two-way diaphragm in accordance with certain embodiments.

Turning now to FIG. 6, the operation of the two-way accumulator assembly is shown schematically. A normally closed inlet valve 8 (or 9) is in fluid communication with the inlet port of the accumulator 10 (and the outlet of the reservoir via line 22). A normally closed outlet valve 11 is in fluid communication with the outlet port of the accumulator 10. Miniature solenoid valves are suitable. Preferably the valves 8 (and 9), 11 are controlled electronically, such as through a module programmed by an external programmer. The outlet of the accumulator 10 communicates with a catheter or the like via a line that delivers the infusate to the delivery site in the patient in a conventional manner.

The diaphragm 40, as illustrated in FIG. 4, is a circular disk of a thin metal sheet. Preferably titanium may be used, although other materials also may be suitable as determined by those skilled in the art. The disk is selected to have a diameter and thickness of low spring rate over the desired range of deflection. Thus, the diaphragm acts as a compliant, flexible wall that separates fluid from the environment behind it. The upward and downward motions of the diaphragm 40 are limited by the bottom surface of the housing 50, and the top surface of the faceplate 56, each of which serves as a mechanical stop for the diaphragm, depending on whether the diaphragm chamber 57 is filled with infusate or is empty of infusate. Thus, these surfaces are provided with a shallow concave profile manufactured into its diaphragm contact surface. This surface acts as a contour stop for the diaphragm. Dimensions of the contour are chosen to match the general profile of the diaphragm when it is deflected or biased by a predetermined fixed volume. This predetermined fixed volume is the volume desired to be metered from the accumulator (e.g., 2 µl).

Deflection of the diaphragm 40 occurs in both the upward and downward direction. The fixed volume pumped is essentially twice that pumped by a diaphragm of the same size that is only deflected in one direction in the same accumulator package configuration. Thus, the two-way diaphragm permits the optimization of accumulator size and energy utilization to increase fixed volume pumping and to conserve battery energy. The first step in the FIG. 6 pumping cycle shows the accumulator 10 in a state where the inlet valves 8 (and 9) and the outlet valve 11 are closed, and the diaphragm chamber 57 of the accumulator is empty (i.e., devoid of infusate fluid). In this condition, preferably the diaphragm 40 is firmly held against the spacer 70 by the gas and is substantially flat; it is not being urged or deflected in either an upward or downward direction (it is noted that the accumulator pressure is generally less than the reservoir pressure and diaphragm spring force and greater than the catheter outlet pressure). The second step in the cycle shows the accumulator 10 after an inlet valve 8 has been opened (maintaining the outlet valve 11 closed). The infusate fluid overcomes the bias of the pressurized gas against the diaphragm 40, and deflects the diaphragm 40 upward, thereby filling the diaphragm chamber 57 with fluid from the reservoir. The third step in the cycle is the closing of the inlet valve 8 once the diaphragm chamber 57 has been filled to its fixed or desired volume. The fourth step (not shown) is the opening of the inlet valve 9, if the reservoir with which it communicates contains infusate, followed by the closing of the inlet valve 9 once the desired volume of such infusate has entered the accumulator. The final step in the cycle is the opening of the outlet valve 11 (while maintaining the inlet valves 8 and 9 in the closed position) to empty the diaphragm chamber 57 through the catheter 36, wherein the diaphragm 40 deflects downward as a result of the bias from the gas pressure in the gas chamber 52 and in the gas side of the diaphragm chamber 57. Accordingly, the diaphragm 40 deflects in a first direction during the filling operation of the accumulator 10, as infusate fluid under pressure forces the diaphragm upwards against the mechanical stop of the bottom surface of the housing 50, overcoming the pressure exerted by the gas in the accumulator. The diaphragm also deflects in a second direction during the emptying of the accumulator 10, past its flat, resting point position, as the pressurized gas in the accumulator forces the diaphragm downward against the mechanical stop of the top surface of the faceplate 56. The two-way deflection allows twice the volume to be delivered during a single pumping cycle compared to conventional designs, using the substantially same amount of energy. Preferably the first and second directions of deflection of the diaphragm are opposite directions. The accumulator 10 thus stores and discharges predetermined volume spikes of infusate at a frequency defined by the cycling rate of the inlet and outlet valves.

Since the metering assembly controls the flow of fluid from the reservoir and does not rely on constant pressure to initiate flow, although a two-phase liquid can be used in the reservoir, a one-phase gas is suitable as well. Suitable gasses include inert gases such as argon, helium and nitrogen, mixtures thereof, and air.

The spacer 70 in accordance with certain embodiments of the present invention improves upon the prior art with a design that maximizes the wash out of fluid and minimizes dead volume. Channels in the spacer are designed to create a flow path that allows the fluid to exit the accumulator quickly (e.g., the channel flow restriction is kept large enough to allow the accumulator to empty in a short period of time). It was found that the multiple annular grooves of the prior art provided multiple sites for stagnant fluid and air encapsulation resulting in dead volume and a degradation of pumping accuracy. As seen in FIG. 5, the spacer 70 of the present invention includes an annular groove 54 intersected by (and thereby in fluid communication with) a trough 53 connecting the inlet and outlet valves wherein the volume of the space created by the annular and trough grooves permits the dead volume in the grooves and outlets to be equal to or less than about 5% of the total volume discharged by the accumulator. Preferably only a single annular groove 54 is provided, and it is interior to the inlet and outlet apertures respectively communicating with the inlet and outlet valves, such that the diameter of the annular groove 54 is smaller than the length of the trough 53. The groove 54 thus provides an annular flow path, and the trough 53 provides a lateral flow path between the inlet and outlet of the accumulator. Fluid in the groove 54 thus communicates with the inlet and outlet of the accumulator only through communication with the trough 53. The remaining peripheral surface of the space plate 50 is preferably flat. The new design flow path configuration and placement also allows for the fluid to flow out of the accumulator without adversely affecting the empty time.

The valves of the metering system can be controlled electronically via a battery powered module utilizing an external programmer. The metering system can also be controlled directly by the external programmer. Dosing can be effected through medication administered from a single or a combination of reservoirs and medications can be mixed or diluted in the accumulator before administration to a patient.

Figure 3:
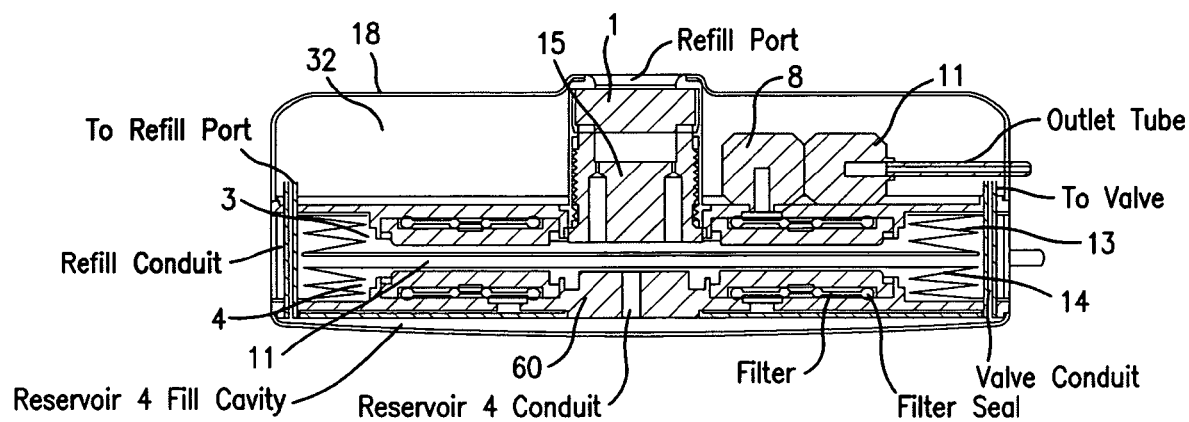
FIG. 3 is a cross-sectional view of the implantable infusion device in accordance with certain embodiments.

Turning now to FIG. 3, the implantable portion of the system is illustrated in cross section. The implantable portion includes a housing 18 containing the reservoirs 3, 4 respectively defined by bellows 13, 14, the two-phase pump chamber 11 containing propellant, an electronics cavity, and the accumulator valve aspects of the system. The pump reservoirs can be periodically accessed transcutaneously via the reservoir septums 1, 2 (only one shown). The septums can be stressed elastomer seals, which may be punctured with a needle. They are self-sealing for a finite number of punctures. Reservoir 4 fill cavity is an annular chamber located below the bellows substrate, and is in fluid communication with the reservoir 4 via a reservoir 4 conduit as shown, providing fluid access to the reservoir 4 to fill the same. The reservoirs 3, 4 (and the bellows 13, 14 that define them) preferably are positioned in a common pressure chamber 11 as shown. Both reservoirs are preferably within close proximity to each other such that either reservoir can independently expand to fill the chamber 11 volume or both reservoirs can expand to such that the combined volume of each reservoir fills the chamber 11.

Figure 2:
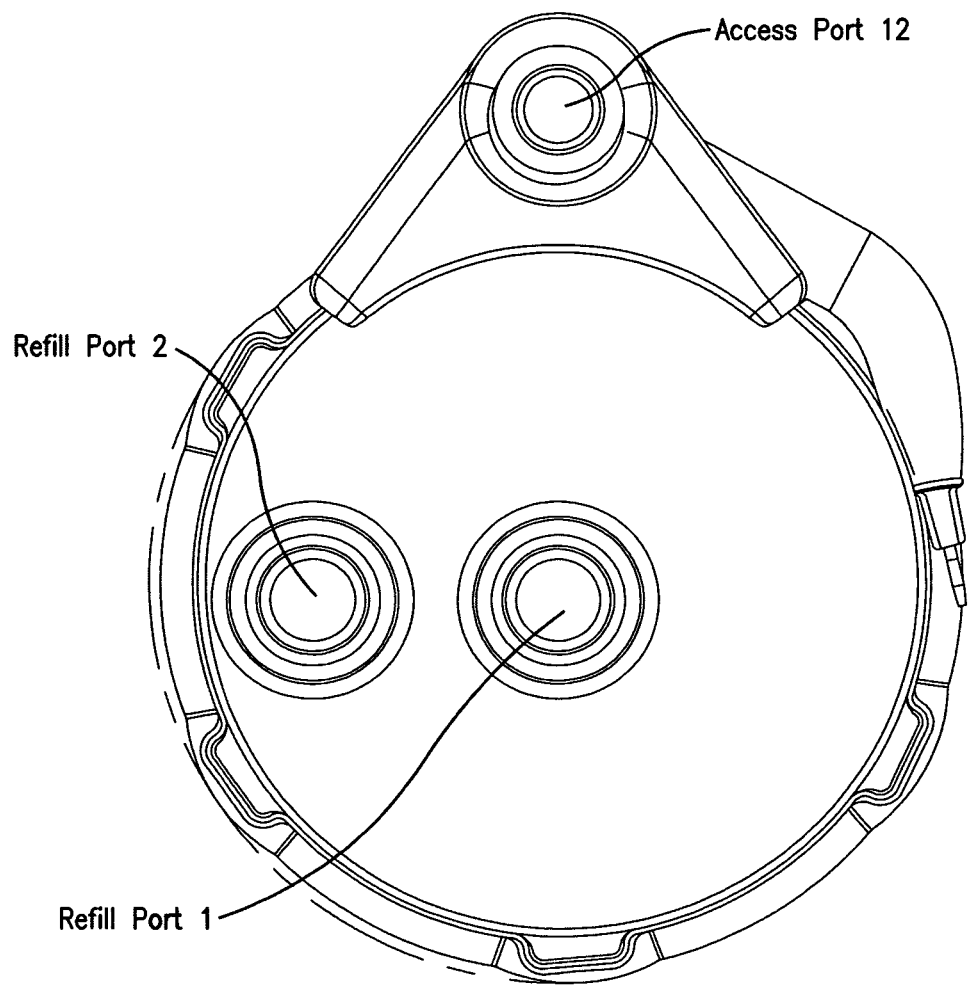
FIG. 2 is a top view of the implantable infusion device in accordance with certain embodiments.

As illustrated in FIGS. 2 and 3, the mechanical construction of the device comprises a hollow disk-shaped housing generally made of two components comprising a lower section and an upper or cover section. The two main cavities of the system are separated by a solid base plate 60, which defines the central core of the unit.

The central core region contains the needle piercing septums 1, 2 through which drug is injected into the bellows chambers. The septums each include a needle-stop 15 to limit the travel of the needle without damaging the needle.

The system includes within the housing 18, the electronics cavity 32 containing the necessary microprocessor electronics and battery. Battery life is sufficient to power the device during its normal intended implantable life. The housing 18 includes within the central core region the valves 8, 9 and 11 and the accumulator 10. The valves can comprise miniature solenoid valves that are connected to the accumulator 10.

What is claimed is:

1. A method of independently introducing infusate into an accumulator from at least two separate infusate sources, comprising:

providing an implatable pressure chamber that contains a fluid having positive vapor pressure at normal body temperature;

providing a first infusate reservoir in said pressure chamber, said first infusate reservoir adapted to contain a first infusate at a constant pressure of the pressure chamber;

providing an additional infusate reservoir in said pressure chamber, said additional infusate reservoir adapted to contain an additional infusate at a constant pressure of the pressure chamber, wherein the additional infusate reservoir is oppositely disposed to the first infusate reservoir in the pressure chamber;

providing a metering assembly consisting essentially of a fixed volume accumulator having an inlet in fluid communication with said first infusate reservoir via a first valve and in fluid communication with said additional infusate reservoir via an additional valve, and an outlet valve in communication with an outlet of said accumulator, said accumulator comprising a chamber housing a flexible diaphragm that provides a barrier between a gas portion of the chamber and an infusate portion of the chamber;

introducing said first infusate into said first infusate reservoir to cause the first reservoir to expand in a first direction;

introducing said additional infusate into said additional infusate reservoir to cause the additional infusate reservoir to expand in a second direction opposite the first direction;

introducing said first infusate from said first infusate reservoir independent of said additional infusate into said infusate portion of said accumulator by opening said first valve while said additional valve and said outlet valve are in a closed position;

emptying said accumulator of said first infusate by opening said outlet valve while said first and additional valves are closed;

introducing said additional infusate from said additional infusate reservoir into said infusate portion of said accumulator by opening said additional valve while said first valve and said outlet valve are in a closed position; and emptying said additional infusate from said accumulator by opening said outlet valve while said first and additional valves are in a closed position.

2. The method of claim 1, wherein said first infusate reservoir is filled with said first infusate, and said accumulator is filled with and then emptied of said first infusate, multiple times before said additional infusate is introduced into said additional infusate reservoir.

3. The method of claim 1, wherein introducing said first infusate from said first infusate reservoir independent of said additional infusate into said accumulator further comprises channeling said first infusate through said accumulator through a single trough providing a lateral flow path between said inlet and outlet of said accumulator and an annular groove intersecting said trough with a diameter less than a length of said trough providing an annular flow path.

4. The method of claim 1, wherein introducing said second infusate from said additional infusate reservoir independent of said first infusate into said accumulator further comprises channeling said additional infusate through said accumulator through a single trough providing a lateral flow path between said inlet and outlet of said accumulator and an annular groove intersecting said trough with a diameter less than a length of said trough providing an annular flow path.

* * * * *